(12) United States Patent
Chouinard

(10) Patent No.: US 6,709,455 B1
(45) Date of Patent: *Mar. 23, 2004

(54) STENT-GRAFT-MEMBRANE AND METHOD OF MAKING THE SAME

(75) Inventor: Paul F. Chouinard, Roseville, MN (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/687,165

(22) Filed: Oct. 10, 2000

Related U.S. Application Data

(62) Division of application No. 09/134,859, filed on Aug. 14, 1998, now Pat. No. 6,156,064.

(51) Int. Cl.$^7$ ............................... A61F 2/10; A61F 2/06
(52) U.S. Cl. ..................................... 623/1.32; 623/1.13
(58) Field of Search .......................... 623/1.13, 1.14, 623/1.16, 1.23, 1.32, 1.27, 1.35, 1.39, 1.4, 1.44, 1.46, 1–49, 1.54

(56) References Cited

U.S. PATENT DOCUMENTS

| | | | |
|---|---|---|---|
| 4,475,972 A | 10/1984 | Wong | 156/167 |
| 4,604,762 A | 8/1986 | Robinson | 623/1 |
| 4,655,771 A | 4/1987 | Wallstén | 623/1 |
| 4,743,252 A | 5/1988 | Martin, Jr. et al. | 623/1 |
| 4,810,749 A | 3/1989 | Pinchuk | 524/730 |
| 4,850,999 A | 7/1989 | Planck | 623/1 |
| 4,954,126 A | 9/1990 | Wallstén | 600/36 |
| 5,061,275 A | 10/1991 | Wallstén et al. | 623/1 |
| 5,084,065 A | 1/1992 | Weldon et al. | 623/1 |
| 5,116,360 A | 5/1992 | Pinchuck et al. | 623/1 |
| 5,133,742 A | 7/1992 | Pinchuk | 623/1 |
| 5,534,287 A | 7/1996 | Lukic | 427/2.25 |
| 5,591,226 A | 1/1997 | Trerotola et al. | 623/1 |
| 5,628,788 A | 5/1997 | Pinchuk | 623/1 |
| 5,639,278 A | 6/1997 | Dereume et al. | 623/1 |
| 5,645,559 A * | 7/1997 | Hatchman et al. | 606/198 |

(List continued on next page.)

FOREIGN PATENT DOCUMENTS

| | | |
|---|---|---|
| WO | 8002641 | 12/1980 |
| WO | 9406373 | 3/1994 |
| WO | 9424961 | 11/1994 |

OTHER PUBLICATIONS

U.S. patent application Ser. No. 08/598,751 entitled *"Titanium Alloy Self–Expanding Stent"*, filed Apr. 30, 1996, which is commonly owned by the assignee of the above-captioned application.

(List continued on next page.)

*Primary Examiner*—Corrine McDermott
*Assistant Examiner*—Hieu Phan
(74) *Attorney, Agent, or Firm*—Larkin Hoffman Daly & Lindgren Ltd.; Frederick W. Niebuhr

(57) ABSTRACT

A braided self-expandable stent-graft-membrane made of elongated members forming a generally tubular body. A membrane layer and graft layer are disposed on a endoprosthesis such as a stent. The membrane layer is substantially impermeable to fluids. The outermost layer is biocompatible with the body tissue. The innermost layer is biocompatible with the fluid in the passage. An embodiment includes a graft layer disposed on the inside of a stent and a membrane layer disposed on the outside of the stent. The innermost layer is biocompatible with the fluid in the passage. The stent-graft-membrane is used at a treatment site in a body vessel or organ where it is desirous to exclude a first fluid located outside the endoprosthesis from reaching a second fluid located in the lumen. The membrane may be made of silicone or polycarbonate urethane. The graft may be braided, woven, spun or spray-cast PET, PCU, or PU fibers. The layers may include ePTFE or PTFE.

29 Claims, 11 Drawing Sheets

U.S. PATENT DOCUMENTS

| | | | | |
|---|---|---|---|---|
| 5,653,747 A | * | 8/1997 | Dereume | 623/1 |
| 5,679,470 A | | 10/1997 | Mayer | 428/662 |
| 5,718,159 A | * | 2/1998 | Thompson | 87/33 |
| 5,735,897 A | | 4/1998 | Buirge | 623/12 |
| 5,741,333 A | | 4/1998 | Frid | 623/12 |
| 5,755,774 A | | 5/1998 | Pinchuk | 623/1 |
| 5,758,562 A | | 6/1998 | Thompson | 87/33 |
| 5,788,626 A | | 8/1998 | Thompson | 600/36 |
| 5,800,512 A | | 9/1998 | Lentz et al. | 623/1 |
| 5,904,967 A | * | 5/1999 | Ezaki et al. | 428/36.92 |
| 6,001,125 A | * | 12/1999 | Golds et al. | 623/23.7 |
| 6,156,064 A | * | 12/2000 | Chouinard | 623/1.44 |
| 6,217,609 B1 | * | 4/2001 | Haverkost | 623/1.22 |

OTHER PUBLICATIONS

U.S. patent application Ser. No. 08/640,253 entitled "*Cobalt–Chromium–Molybdenum Alloy Stent Graft*", filed Apr. 30, 1996, which is commonly owned by the assignee of the above–captioned application.

U.S. patent application Ser. No. 08/904,467, entitled "*Bioabsorbable Self–Expanding Stent*", filed Aug. 1, 1997, which is commonly owned by the assignee of the above-captioned application.

U.S. patent application Ser. No. 08/946,906, entitled "*Stent Graft with Braided Polymeric Sleeve*", filed Oct. 8, 1997, which claims the benefit of U.S. Provisional patent application Ser. No. 60/036,160, filed Jan. 23, 1997 and is commonly owned by the assignee of the above–captioned application.

U.S. patent application Ser. No. 08/993,985, entitled "*Stent-Graft with Bioabsorbable Structural Support*", filed Dec. 18, 1997, which is commonly owned by the assignee of the above–captioned application.

* cited by examiner

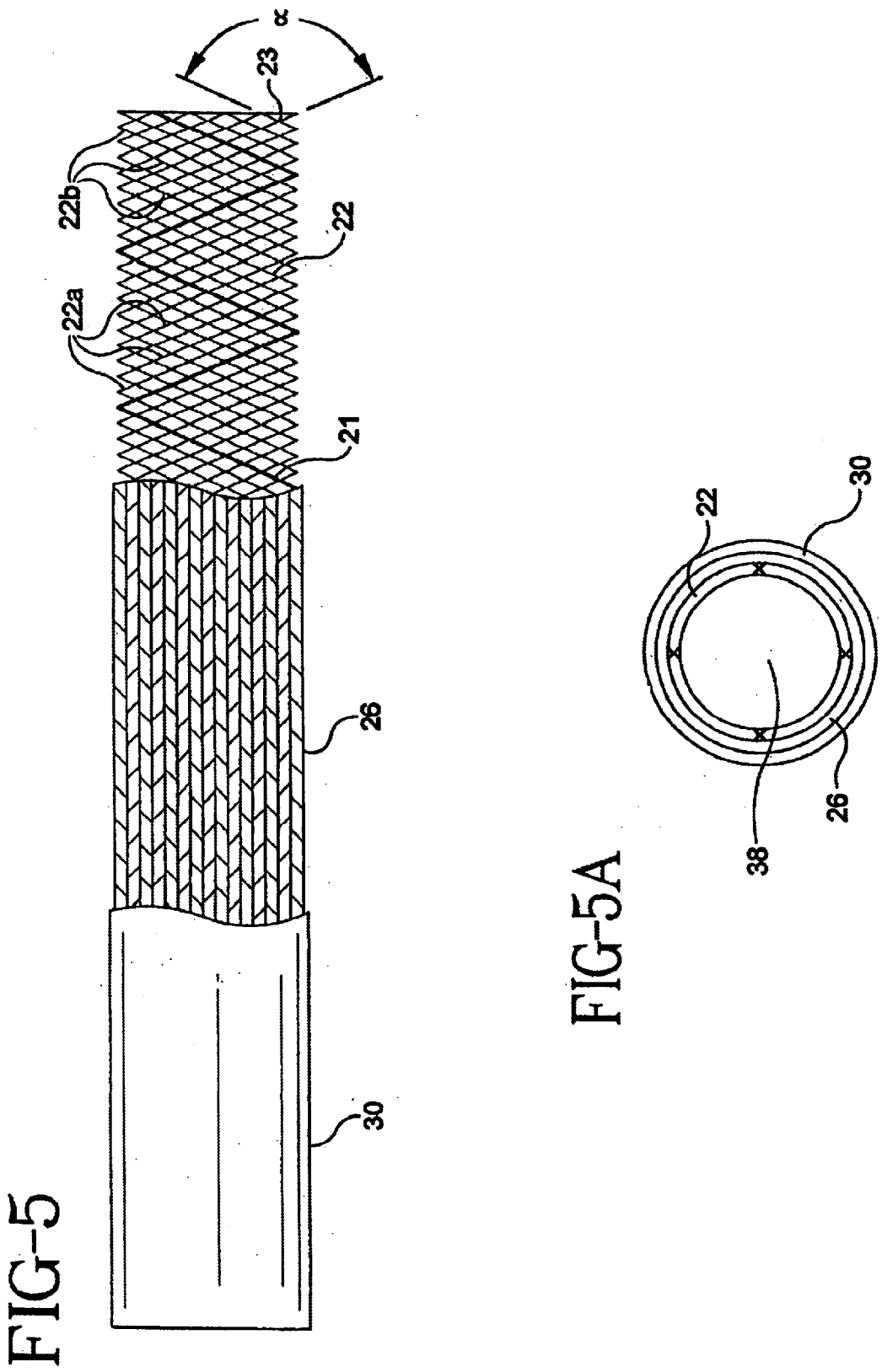

STENT-GRAFT-MEMBRANE AND METHOD OF MAKING THE SAME

This application is a division of application Ser. No. 08/134,859, filed Aug. 14, 1998, now U.S. Pat. No. 6,156,064.

FIELD OF THE INVENTION

The present invention relates to a stent-graft-membrane for placement at a treatment site within a body vessel or organ to enhance and direct fluid flow therethrough and a method of making the same. More particularly, the invention relates to an implantable endoprosthesis such as a stent combined with a generally impermeable membrane layer and a permeable graft layer. The graft and the membrane provide biocompatibility with tissue at the treatment site and provide biocompatibility with fluid in the lumen.

BACKGROUND OF THE DISCLOSURE

Intraluminal implantable endoprostheses such as self expanding stents, grafts and stent-grafts are known and are, for example, shown in U.S. Pat. Nos. B1 4,954,126; 5,116,360; 5,133,742; 5,591,226; 5,653,747; and 5,679,470. A covered stent is described in International Publication Number WO 94/24961. A polyurethane is described in U.S. Pat. No. 4,810,749. A porous implantable material is described in U.S. Pat. No. 4,475,972. A method of forming an implantable graft is described in U.S. Pat. No. 4,738,740.

U.S. Pat. No. B1 4,655,771, entitled, Prosthesis Comprising Expansible or Contractile Tubular Body, discloses a prosthesis comprising a flexible tubular body for tansluminal implantation.

U.S. Pat. No. 5,061,275, entitled, Self-Expanding Prosthesis, discloses a resilient, elastic self-expanding prosthesis comprising a flexible tubular body.

U.S. Pat. No. 5,645,559, entitled, Multiple Layer Stent, discloses a radially self-expanding stent having multiple layers that includes a medial region and proximal and distal cuffs having diameters greater than the medial region diameter when the stent is in the relaxed state. A silicone coating circumscribes at least the medial region of the stent.

U.S. Pat. No. 5,718,159, entitled, Process for Manufacturing Three-Dimensional Braided Covered Stent, discloses a prosthesis having a flexible tubular three-dimensionally braided structure of metal or polymeric non-filaments, and polymeric multifilament yarns.

U.S. Pat. No. 5,741,333, entitled, Self-Expanding Stent For A Medical-Device To Be Introduced Into A Cavity Of A Body, discloses a self-expanding stent.

U.S. Pat. No. 5,755,774, entitled, Bistable Luminal Graft Endoprosthesis, discloses a luminal graft endoprosthesis or endovascular graft which is capable of dilation and support functions and suitable for the endoluminal repair of vascular lesions and the like. An expandable support or stent is combined with a tubular graft made of a material having two unstressed conditions to provide a combined stent-graft wherein the graft material is secured to either or both of the internal or external surfaces of the stent.

U.S. Pat. No. 5,534,287, entitled, Methods for Applying an Elastic Coating Layer on Stents, discloses a coated stent comprising a cylindrical wall formed by meshed wires and a covering layer of elastic material extending on a portion of its length, with an outer surface, and totally embracing the wire mesh.

U.S. Pat. No. 4,850,999, entitled, Flexible Hollow Organ, discloses a flexible hollow organ, especially a vascular prosthesis intended for implantation in the human or animal body parts. The hollow organ includes a flexible prosthetic tube serving for a throughflow of a medium or which consists of such a prosthetic tube. A wall of the prosthetic tube exhibits at least one braided hose of flexible, elastic threads produced as a hollow meshwork.

A stent-graft is described in U.S. patent application Ser. No. 08/640,253, entitled "Cobalt-Chromium-Molybdenum Alloy Stent and Stent Graft", filed Apr. 30, 1996.

A stent-graft is described in U.S. patent application Ser. No. 08/993,985, entitled, Stent-Graft with Bioabsorbable Structural Support, filed Dec. 18, 1997.

A stent-graft is described in U.S. patent application Ser. No. 08/946,906 entitled, Stent-Graft with Braided Polymeric Sleeve, filed Oct. 8, 1997.

All references cited herein are incorporated herein by reference in their entireties for all purposes.

SUMMARY OF THE INVENTION

The stent-graft-membrane of the present invention has at least three layers and is intended for treatment of vascular lumens, non-vascular lumens or organs in the body. The three layers include a structural stent layer a raft layer and a membrane layer. The three layers may be formed in different combinations of layers. A need exists for a stent-graft-membrane of the present invention having layers with surfaces that are selected to be biocompatible with the tissue or fluid for which they are associated with while treating vessels or organs. Biocompatibility means that the implant is accepted by the host tissue and does not create an adverse biological response.

The stent-graft-membrane may advantageously be used in a variety of medical applications including intravascular treatment of stenoses, aneurysms or fistulas; maintaining openings in the urinary, biliary, tracheobronchial, esophageal, renal tracts, vena cava filters; repairing abdominal aortic aneurysms; or repairing or shunting damaged or diseased organs.

In sum, the invention relates to an implantable endoprosthesis including a first number of elongated members wound helically in a first common direction and crossing a second number of elongated members wound helically in a second common direction. The crossing of the first and second elongated members define an angle and form a generally tubular body having an inside surface, outside surface, ends and a middle portion. The first and second elongated members are braided in a braid pattern and are configured to be constrainable to a reduced diameter and self-expandable to an increased diameter. The tubular body is disposed at a treatment site in a body vessel or organ having body tissue. A passage extends in a longitudinal direction at least partially through the generally tubular body. The passage at least partially contains a fluid in the lumen and directs flow. One or more outside layers are disposed over or on at least a portion of the outside surface of the tubular body. An outermost layer of the one or more outside layers is biocompatible with the body tissue. One or more inside layers are disposed over or on at least a portion of the inside surface of the tubular body. An innermost layer of the one or more inside layers is biocompatible with the fluid in the passage. At least one of the one or more outside layers or the one or more inside layers are substantially impermeable to fluids. The inside layer or the outside layer may each include one or more layers. The one or more inside and outside layers may include one or more membrane layers having an average permeability ranging from about 0 cc/cm$^2$/min. to about 100 cc/cm$^2$/min. and/or one or more graft layers having an average permeability ranging from about 50 cc/cm$^2$/min. to about 5000 cc/cm$^2$/min. The outside layer may be a film or membrane made of silicone or polycarbonate urethane and the inside layer may be a graft made of braided PET. The inside layer may be ePTFE or PTFE. The implantable endoprosthesis may be designed to provide structural structural support to a body vessel for a period of time and substantially separate a first body fluid located outside the endoprosthesis from a second body fluid located in the passage. The implantable endoprosthesis may be disposed at a Transjugular Intrahepatic Portosystemic Shunt (TIPS) treatment site. At a TIPS treatment site, the first fluid may include bile and the second fluid may include blood. The braided implantable endoprosthesis may include an opening defined by each end of the generally tubular body. The tubular body may be made of metal, plastic, bioabsorbable or other synthetic or natural materials. The tubular body may have a braid angle or filament crossing angle of between about 65 degrees and 155 degrees.

The invention also relates to an implantable endoprosthesis including a first set of filaments each of which extends in a configuration along a center line and having a first common direction of winding. A second set of filaments each extends in a configuration along a center line and having a second common direction of winding. The first and second filaments form a stent. One or more membrane layers having a first average permeability are disposed over or on at least one of an inside, interstices, or outside surface of the stent or a graft. One or more graft layers having a second average permeability are disposed over or on at least an inside, interstices, or outside surface of the stent. The first and second set of filaments, and the one or more membrane layers and graft layers form a self expanding structure having one or more layers including an inside layer, middle layer, outside layer, embedded layers or combinations thereof, inside surface, outside surface, proximal end, distal end, and a lumen. The inside surface is selected or configured to be substantially biocompatible with a fluid flow through the body lumen and the outside surface is selected or configured to be substantially biocompatible with a body tissue. The first average permeability may be less than the second average permeability. The one or more membrane layers may have an average permeability ranging from about 0 cc/cm$^2$/min. to about 100 cc/cm$^2$/min., and the one or more graft layers may have an average permeability ranging from about 50 cc/cm$^2$/min. to about 5000 cc/cm$^2$/min. The one or more graft layers may include polyethylene terephthalate (PET), expanded polytetrafluoroethylene (ePTFE), polycarbonate urethane (PCU), polyurethane (PU), or combinations thereof. The one or more membrane layers may include siloxane polymers, polyurethane polymers, polycarbonate urethanes, PTFE, ePTFE, or combinations thereof. The one or more membrane layers may be disposed between the graft and the stent. The one or more graft layers may be disposed between the membrane and the stent. The stent may be disposed between the one or more membrane layers and the one or more graft layers. The layers may be bonded with an adhesive. The stent may be made of poly (alpha-hydroxy acid), PGA, PLA, PLLA, PDLA, polvcaprolactone, polydioxanone, polygluconate, polylactic acid-polyethylene oxide copolymers, modified cellulose, collagen, poly (hydroxybutyrate), polyanhydride, polyphosphoester, poly (amino acids), or combinations thereof. The filaments may include Elgiloy®, stainless steel, nitinol, drawn filled tube (DFT), platinum, tungsten, tantalum, or combinations thereof. The graft layers may include a plurality of interwoven fibers, mono-filaments, multi-filaments, or yarns. The membrane layers may include a film, sheet, or tube. The implantable endoprosthesis may substantially exclude a first fluid located outside the surface of the implantable endoprosthesis from reaching a second fluid located in the lumen. The inside layer may be made of a PET polymer. The outside layer may be made of a silicone elastomer. The silicone elastomer may be a coating. The outside layer may be made of a polymer that is resistant to fluid permeability or resistant to tissue ingrowth.

The invention also relates to a method of making a stent-graft-membrane including: forming a first number of elongated members wound helically in a first common direction and crossing a second number of elongated members wound helically in a second common direction. The crossing of the first and second elongated members define an angle and form a generally tubular body having an inside surface, outside surface, ends and a middle portion. The first and second elongated members are braided in a braid pattern and are designed to be constrainable to a reduced diameter and self-expandable to an increased diameter. The tubular body is adapted to be disposed at a treatment site in at least one of a body vessel or organ having body tissue; forming a passage extending in a longitudinal direction at least partially through the generally tubular body. The passage is adapted to at least partially contain a fluid; forming one or more outside layers on at least a portion of the outside surface of the tubular body. An outermost layer of the outside layers is biocompatible with the body tissue; forming one or more inside layers on at least a portion of the inside surface of the tubular body. An innermost layer of the inside layers is biocompatible with the fluid in the passage. At least one of the outside layers or the inside layers is substantially impermeable to a fluid.

The invention also relates to a method of making a stent-graft-membrane including: braiding bioabsorbable filaments to form a tubular braid. The braid having a braid angle; disposing the braid on a mandrel; annealing the braid for a predetermined time to form an annealed stent; removing the stent from the mandrel, the stent having a filament crossing angle; forming a craft having a an average permeability ranging from about 50 cc/cm$^2$/min. to about 5000 cc/cm$^2$/min. on at least one of an inside or outside surface of the stent; adhering at least a portion of the graft to the stent; and forming a membrane having an average permeability ranging from about 0 cc/cm$^2$/min. to about 100 cc/cm$^2$/min. on at least a portion of the stent. The method of making a stent-graft-membrane may further include prior to the step of adhering, applying a thermoplastic adhesive, curable adhesive, or bioabsorbable polymer adhesive to a surface of the stent or to a surface of the graft.

The invention also relates to an implantable endoprosthesis including a first number of elongated members wound helically in a first common direction and crossing a second number of elongated members wound helically in a second common direction. The crossing of the first and second elongated members define an angle and form a generally tubular body having an inside surface, outside surface, ends and a middle portion therebetween. The first and second elongated members are braided in a braid pattern and are configured to be constrainable to a reduced diameter and self-expandable to an increased diameter. The tubular body is adapted to be disposed at a treatment site in at least one of a body vessel or organ having body tissue. A passage extends in a longitudinal direction at least partially through the tubular body. The passage is adapted to at least partially contain a fluid. One or more outside layers are disposed over at least a portion of the outside surface of the tubular body. At least one of the outside layers is a membrane made of a silicone or a polycarbonate urethane material biocompatible with the body tissue. One or more inside layers are disposed over at least a portion of the inside surface of the tubular body. At least one of the inside layers is a graft made of braided PET material biocompatible with the fluid in the passage. The implantable endoprosthesis is configured such that at least one of the outside layers is substantially impermeable to a fluid and substantially separates a first body fluid located outside the endoprosthesis from a second body fluid located in the passage. A first end portion of the implantable endoprosthesis may be disposed in a portal vein and the other end portion of the implantable endoprosthesis may be disposed in a hepatic vein. A middle portion of the braided implantable endoprosthesis may be disposed in a liver. The first fluid may be bile and the second fluid may be blood.

A preferred use includes placing the stent-graft-membrane through a liver. Transjugular Intrahepatic Portosystemic Shunt (TIPS) is formed by an intrahepatic shunt connection between the portal venous system and the hepatic vein for prophylaxis of variceal bleeding, in the treatment of portal hypertension and its complications. Portal hypertension causes blood flow to be forced backward, causing veins to enlarge, resulting in variceal bleeding. The stent-graft-membrane advantageously acts as a shunt to enable blood to flow through the liver to the hepatic vein. The shunt generally decompresses portal hypertension and allows veins to shrink to normal size, stopping the variceal bleeding.

The invention also relates to a method of using a stent-graft-membrane comprising the steps: identifying a treatment site; determinig the tissue, organ or fluid at the treatment site that the inside surface and the outside surface of the stent-graft-membrane are to be associated with; determining one or more materials for the inside and outside surfaces of the stent-graft-membrane that are substantially biocompatible with the tissue, organ or fluid at the treatment site; providing a stent-graft-membrane. The stent-graft-membrane having a first number of elongated members wound helically in a first common direction and crossing a second number of elongated members wound helically in a second common direction. The crossing of the first and second elongated members defining an angle therebetween and forming a generally tubular body having an inside surface, outside surface, ends and a middle portion therebetween. The first and second elongated members are braided in a braid pattern and are configured to be constrainable to a reduced diameter and self-expandable to an increased diameter. The generally tubular body is adapted to be disposed at a treatment site in at least one of a body vessel or organ having body tissue. A passage extends in a longitudinal direction at least partially through the generally tubular body. The passage is adapted or configured to at least partially contain a fluid. One or more outside layers are disposed over or on at least a portion of the outside of the tubular body. An outermost layer of the one or more outside layers is substantially biocompatible with the body tissue. One or more inside layers are disposed over or on at least a portion of the inside of the tubular body. An innermost layer of the one or more inside layers is substantially biocompatible with the fluid in the passage. At least one of the one or more outside layers or the one or more inside layers are substantially impermeable to fluids; inserting the stent-graft-membrane in a delivery device; inserting the delivery device into a body and delivering the stent-graft-membrane and at least a portion of the delivery device to the treatment site; and deploying the stent-graft-membrane into a position at the treatment site.

In the design of an implantable medical device such as a stent-graft-membrane, it is important that each of the component materials be biocompatible with the host tissue. Thus, an implantible medical device should accomplish its intended functional purpose in the body, and should generally not cause an unfavorable reaction in the tissue with which it interacts.

Biocompatibility requirements may vary for different components of an implantible device. For example, in the case of an implant which is placed in a blood vessel, the inside surface of the implant must be biocompatible with the blood flowing through the lumen. Also, the outside surface of the implant must be biocompatible with the tissue of the blood vessel.

For example, in the case of a TIPS stent-graft-membrane, the general purpose of the stent-graft-membrane is to maintain a shunt for blood flow between the portal and hepatic veins. Each component in the stent-graft-membrane has a function which contributes to the general purpose of the device. In a TIPS application, the functional requirement of the stent is to mechanically hold the liver tissue open to maintain the shunt lumen. The functional requirement of the outer membrane is to prevent any inter-mixing of the bile, which is produced by the liver, into the blood which is flowing through the shunt. Inter-mixing of bile and blood may cause the blood to form thrombus. The functional requirement of the inside graft is to provide an interface with the blood which advantageously improves the blood biocompatibilty of the implant.

The stent, graft, or membrane layers may be substantially individual layers that are at least partially bonded together. Alternatively, the stent-graft-membrane may include a stent embedded in the membrane or the membrane embedded in the stent; the stent embedded in the graft or the graft embedded in the stent; and the membrane embedded in the graft or the graft embedded in the membrane. At least one of the stent, graft, or membrane may be embedded in the other.

Each embodiment of the stent-graft-membrane may include a radiopaque tracer wire to make one or more portions more visible during fluoroscopy. Each embodiment of the stent-graft-membrane may include bare filaments at one or more end portions or middle portions.

Still other objects and advantages of the present invention and methods of construction and use of the same will become readily apparent to those skilled in the art from the following detailed description, wherein only the preferred embodiments are shown and described, simply by way of illustration of the best mode contemplated of carrying out the invention. As will be realized, the invention is capable of other and different embodiments and methods of construction and use, and its several details are capable of modification in various obvious respects, all without departing from the invention. Accordingly, the drawings and description are to be regarded as illustrative in nature, and not as restrictive.

BRIEF DESCRIPTION OF THE DRAWINGS

FIG. 5 illustrates a side view of an embodiment of the stent-graft-membrane having a membrane outside layer, graft middle layer, and stent inside layer;

FIG. 5A illustrates an end view of the stent-graft-membrane of FIG. 5;

DETAILED DESCRIPTION OF THE INVENTION

Figure 1:
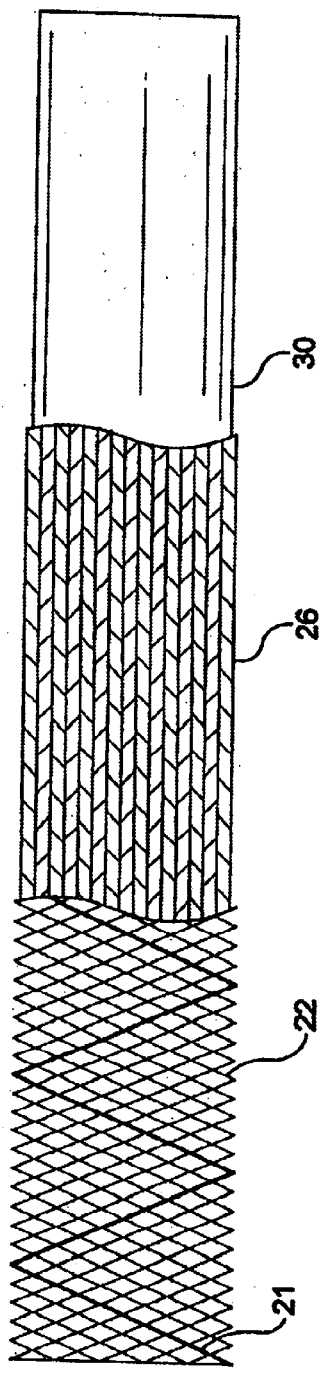
FIG. 1 illustrates a side view of an embodiment of the stent-graft-membrane having a stent outside layer, graft middle layer, and membrane inside layer.
Figure 1A:
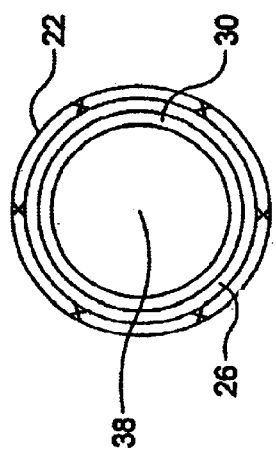
FIG. 1A illustrates an end view of the stent-graft-membrane of FIG. 1.

Reference is made to FIGS. 1–6 showing various embodiments of a stent-graft-membrane 20 with a radiopaque tracer wire 21. FIG. 1 illustrates an embodiment of the stent-graft-membrane 20 with a stent layer 22 located on the outside, a graft layer 26 located in the middle, and a membrane layer 30 located on the inside. FIG. 1A illustrates an end view of the stent-graft-membrane 20 in FIG. 1.

Figure 2:
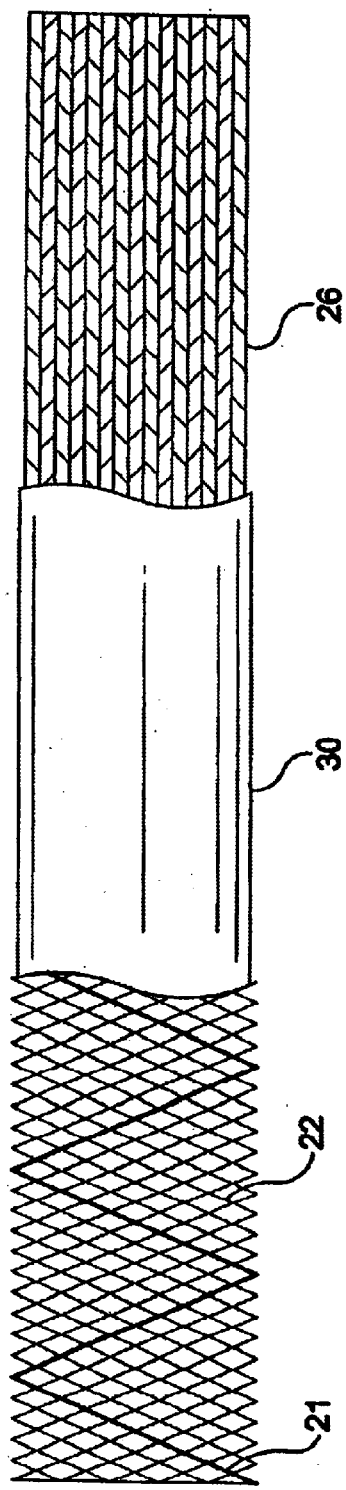
FIG. 2 illustrates a side view of an embodiment of the stent-graft-membrane having a stent outside layer, membrane middle layer, and graft inside layer.
Figure 2A:
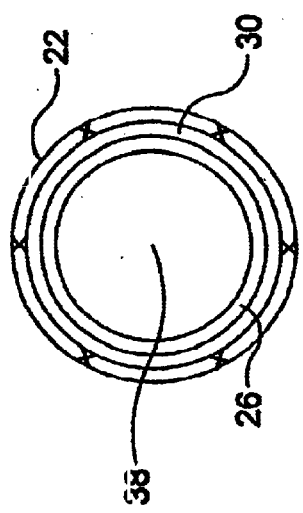
FIG. 2A illustrates an end view of the stent-graft-membrane of FIG. 2.

FIG. 2 illustrates an embodiment of the stent-graft-membrane 20 having a stent layer 22 located on the outside, a membrane layer 30 located in the middle, and a graft layer 26 located on the inside. FIG. 2A illustrates an end view of the stent-graft-membrane 20 of FIG. 2.

Figure 3:
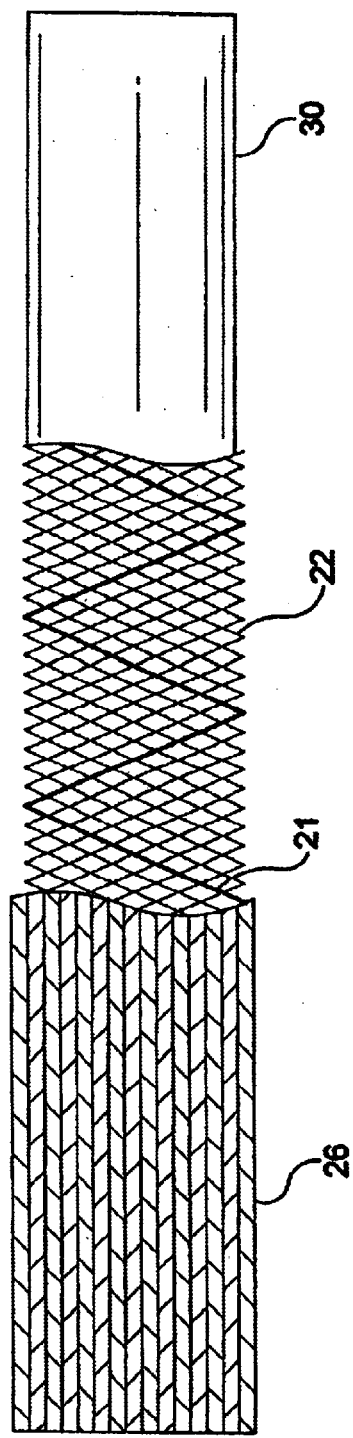
FIG. 3 illustrates a side view of an embodiment of the stent-graft-membrane having a graft outside layer, stent middle layer, and membrane inside layer.
Figure 3A:
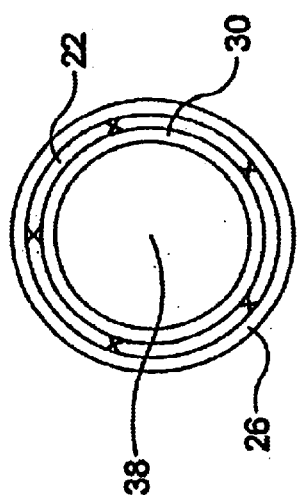
FIG. 3A illustrates an end view of the stent-graft-membrane of FIG. 3.

FIG. 3 illustrates an embodiment of the stent-graft-membrane 20 having a graft layer 26 located on the outside, a stent layer 22 located in the middle, and a membrane layer 30 located on the inside. FIG. 3A illustrates an end view of the stent-graft-membrane 20 of FIG. 3.

Figure 4:
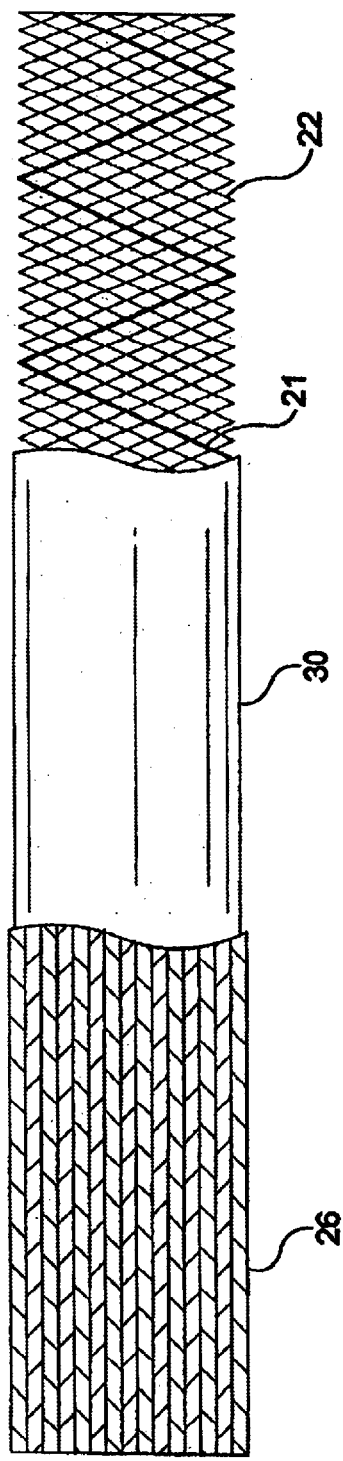
FIG. 4 illustrates a side view of an embodiment of the stent-graft-membrane having a graft outside layer, membrane middle layer, and stent inside layer.
Figure 4A:
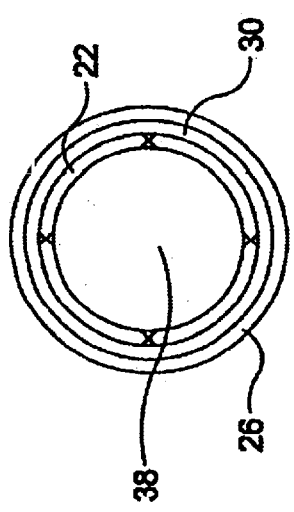
FIG. 4A illustrates an end view of the stent-graft-membrane of FIG. 4.

FIG. 4 illustrates an embodiment of the stent-graft-membrane 20 having a graft layer 26 located on the outside, a membrane layer 30 located in the middle, and a stent layer 22 located on the inside. FIG. 4A illustrates an end view of the stent-graft-membrane 20 of FIG. 4.

FIG. 5 illustrates an embodiment of the stent-graft-membrane 20 having a membrane layer 30 located on the outside, a graft layer 26 located in the middle, and a stent layer 22 located on the inside. FIG. 5A illustrates an end view of the stent-graft-membrane 20 of FIG. 5.

Figure 6:
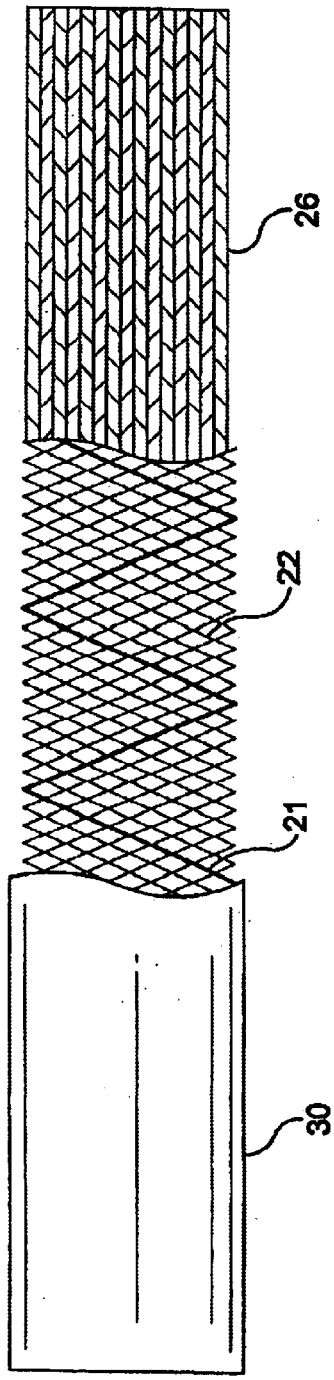
FIG. 6 illustrates a side view of an embodiment of the stent-graft-membrane having a membrane outside layer, stent middle layer, and graft inside layer.
Figure 6A:
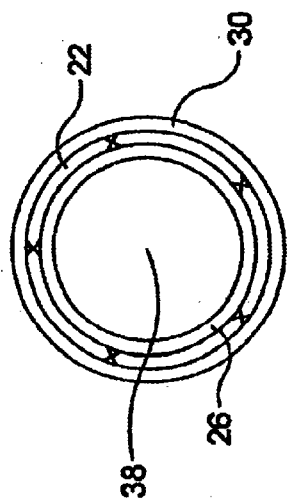
FIG. 6A illustrates an end view of the stent-graft-membrane of FIG. 6.

FIG. 6 illustrates an embodiment of the stent-graft-membrane 20 having a membrane layer 30 located on the outside, a stent layer 22 located in the middle, and a graft layer 26 located on the inside. FIG. 6A illustrates an end view of the stent-graft-membrane 20 of FIG. 6.

General descriptions of the stent 22, graft 26 and membrane 30 include:

A. Stent

The stent is a tubular mesh including interbraided helically-wound filaments. The tubular mesh is capable of a reduction in diameter with a corresponding increase in length. The reduction in diameter facilitates the delivery of the endoprosthesis to the implant site by a deployment catheter. The filaments may include metal having a sufficiently high modulus of elasticity to provide elasticity to the braided structure. The metal structure is age hardened to augment the resiliency of the stent. This results in a self-expanding structure which opens to an expanded diameter when released from a constrained state.

Stent filaments may be made of implantable grade medical stainless steels, Elgiloy®, Conichrome, Phynox, MP35N, nickel/titanium alloys, Nitinol, cobalt-based alloys, CoCrMo, Titanium alloys, titanium-zirconiun-niobium alloys, titanium-aluminum-vanadium alloy known as TI-6A1-4V, drawn filled tube (DFT), platinum, tungsten, tantalum, or combinations thereof.

Stent filaments may also be made of polymers, bioabsorbable polymers, PET, polypropylene, PEEK, HDPE, polysulfone, acetyl, PTFE, FEP, and polyurethane, or combinations thereof.

Stent filaments may also be made of poly (alpha-hydroxy acid), PGA, PLA, PLLA, PDLA, polycaprolactone, polydioxanone, polygluconate, polylactic acid-polyethylene oxide copolymers, modified cellulose, collagen, poly (hydroxybutyrate), polyanhydride, polyphosphoester, poly (amino acids), or combinations thereof.

Average diameters of the filaments may range from about 0.002 inches to about 0.015 inches.

B. Graft

The graft is designed to be compatible with the body tissue or the fluid that it contacts. For example, if the graft is placed on the outside of a stent and is intended for placement in an airway, the graft is made of a material that is compatible with the tissue on the inside of the airway. If the graft is placed on the inside of a stent and is intended for placement in a blood vessel, the graft is made of a material that is compatible with blood.

A preferred embodiment of the graft includes a tubular mesh of interbraided polyethylene terephthalate (PET) yarns. This graft includes two sets of textile strands, helically wrapped in opposite directions around a mandrel in an intertwining pattern to produce a graft which behaves according to approximately the same axial lengthening/diametrical reduction relationship as the stent. Other possible graft structures may include woven or knitted textile grafts and spun-filament grafts. The graft generally has a lower permeability than the stent Textile strands preferably are multifilament yarns, although they can be monofilaments. The textile strands range from about 10 denier to 400 denier. Individual filaments of the multifilament yarns can range from about 0.25 to about 10 denier. Permeability ranges from about 50 cc/cm$^2$/min. to about 5000 cc/cm$^2$/min. at about 120 mmHg differential pressure. The graft layer may be made of spun polycarbonate urethane to create a tubular structure. The graft may have an average wall thickness between about 0.001 and about 0.010 inch.

Graft materials may include PET such as Dacron, ePTFE, polyurethane, polycarbonate urethane, polypropylene, polyethylene such as Spectra, HDPE, silicone, PTFE, and polyolefins.

C. Membrane

The membrane is designed to limit permeability. Permeability is defamed as the ability of fluids to flow through the wall of the stent-graft-membrane. A purpose of the membrane is to further restrict the flow of fluids through the wall of a stent or stent-grant. The membrane can be made by a number of different techniques and a number of different materials. Permeability of the membrane ranges from about 0 cc/cm$^2$/min. to about 100 cc/cm$^2$/min. at 120 mmHg differential pressure. Membrane materials may include siloxane polymers, polyurethane polymers, polycarbonate urethanes, PTFE or ePTFE.

A membrane may be formed on a stent or stent-graft by dipping the stent or stent-graft into a solution including a polymer with a solvent. In this case, the membrane may become embedded in the tent or stent-graft and is generally not a discrete layer. The stent or stent-graft is then removed from the solution, forming a membrane on the stent or stent-graft. The solvent is evaporated from the membrane, and the polymer is cured, if a curable polymer such as silicone is used. The membrane layer may have a thickness between about 0.001 and about 0.010 inch.

A membrane may also be formed by impregnating a porous graft with a polymer. The polymer becomes integrated in the graft interstices, resulting in a graft-membrane which has substantially lower permeability than the graft starting material.

A membrane may also be formed by providing a stent-graft having a stent on the inside layer and a braided PET graft on the outside layer. The stent-graft is placed over a mandrel which has an outer diameter similar to the inner diameter of the stent-graft. The ends of the mandrel are affixed in a machine which rotates the stent-graft and mandrel about a central axis. Using an airbrush or similar spraying apparatus, the stent-graft is sprayed with a solution of silicone in a volatile solvent such as tetrahydrofiran. A volume of 10 cc of silicone solution is sprayed intermittently over a period of approximately fifteen minutes onto the stentgraft. The sprayed stent-graft-membrane and mandrel are placed in an oven at 150° C. for a period of 30 minutes to cure the silicone polymer. After the stent-graft-membrane is formed, the stent, graft and membrane composite is substantially impermeable. An additional graft layer may be bonded on the inside or outside of the stent-graft-membrane depending on biocompatibilty needs. For example, if a silicone has embedded in the graft, the silicone may extend to the inside surface where blood flow occurs. In that case, it may be desirable to add a PET braided graft on the inside for biocompatibilty purposes.

D. Methods for Applying a Membrane to a Stent

1. Dip coating: Dip the stent or stent-graft into polymer dissolved in solvent to coat the stent, then evaporate the solvent (and cure the polymer, if applicable) to form a film.
2. Spray coating: Spray a polymer in solution on to the inside or outside surface of the stent or stent-graft. Then, evaporate the solvent (and curing the polymer, if applicable) to form a film.
3. Apply a polymeric film or tube to the inside and/or outside surface of the stent or stent-graft. Then, fuse the membrane to the stent or stent-graft by use of adhesive, solvent bonding, or by thermal and/or pressure bonding.

EXAMPLE 1

A stent-graft-membrane 20 was made by spraying silicone on a stent-graft. A 10 mm diameter and 50 mm length stent-graft comprising an Elgiloy stent and braided PET graft were bonded together with polycarbonate urethane and placed over a 10 mm diameter mandrel that was first sprayed with a TFE release agent. The mandrel and the stent-graft were placed on a rotational fixture and the motor was turned on to rotate the stent-graft. The stent-graft was coated with a volume of approximately 10 cc of a 6% solid silicone solution. The silicone solution was applied with an airbrush from a distance of approximately 8–10 cm. The solution was applied intermittently over the course of approximately 15 minutes to allow the THF and Xylene solvents to evaporate from the stent-graft surface as it was sprayed in order to prevent the graft from becoming too wet. After the silicone was applied, the mandrel and stent-graft-membrane were placed in an oven at 150° C. for a period of 30 minutes to cure the silicone polymer. After 30 minutes, the stent-graft-membrane was removed from the oven and allowed to cool.

Alternative methods of making the stent-graft-membrane 20 in Example 1 can include: spraying a stent and graft assembly that has not been bonded together with a polymer in solution; spraying the stent-graft with polycarbonate urethane; using a non-coated graft on the inside of stent; or using a mandrel coated with PTFE.

In a preferred embodiment of the stent-graft-membrane 20, a first number of elongated members 22a are wound in a helical pattern in a first common direction and cross a second number of elongated members 22b wound in a helical pattern in a second common direction. As shown in FIG. 5, the crossing point 23 of the first and second elongated members 22a, 22b define an angle an ∞. The elongated members 22a, 22b form a stent 20 having an inside surface, outside surface, ends and a middle portion. The elongated members 22a, 22b are braided in a braid pattern and are constrainable to a reduced diameter and are self-expandable to an increased diameter. An outside layer such as graft layer 26 or membrane layer 30 is disposed over or on at least a portion of the outside surface of the stent 22. The outermost layer is biocompatible with the body tissue. An inside layer such as graft layer 26 or membrane layer 30 is disposed over or on at least a portion of the inside surface of the stent 22. The innermost layer is biocompatible with the fluid in the passage 38. The membrane layer 30 that is located outside or inside the stent 22 is substantially impermeable to fluids. Average permeability of a membrane layer 30 ranges from about 0 cc/cm$^2$/min. to about 100 cc/cm$^2$/min. at 120 mmHg differential pressure and the average permeability of a graft layer 26 ranges from about 50 cc/cm$^2$/min. to about 5000 cc/cm$^2$/min. at 120 mmHg differential pressure. The membrane layer 30 is made of silicone or polycarbonate urethane and the graft layer 26 is made of braided PET. A passage 38 extends in a longitudinal direction at least partially through the stent-graft-membrane 20. The passage 38 is for channeling fluid and for providing a flow direction for the fluid in a vessel or organ.

Another preferred embodiment of the stent-graft-membrane 20 includes a first set of filaments 22a which extend in a configuration along a center line and have a first common direction of winding. A second set of filaments 22b extend in a configuration along a center line and have a second common direction of winding. The first and second filaments 22a, 22b form a stent 22. A membrane layer 30 with a first average permeability is disposed on the inside or the outside of the stent 22. A graft layer 26 with a second average permeability is disposed over or on the inside or the outside of the stent 22. The first and second set of filaments 22a, 22b, membrane layers 30, and graft layers 26 form a self expanding structure having an inside layer, outside layer, and a lumen 38. The membrane layer 30 may be disposed between the graft 26 and the stent 22. The graft layers 26 may be disposed between the membrane 30 and the stent 22. The stent 22 may be outside or inside the graft 26 and membrane 30. The layers 22, 26, 30 may be bonded by an adhesive. The inside layer is biocompatible with a fluid flow through the body lumen and the outside layer is biocompatible with body tissue. The membrane layer 30 has an average permeability ranging from about 0 $cc/cm^2/min.$ to about 100 $cc/cm^2/min.$ at 120 mmHg differential pressure and the graft layer 26 has an average permeability ranging from about 50 $cc/cm^2/min.$ to about 5000 $cc/cm^2/min.$ at 120 mmHg differential pressure. The graft layer 26 may include a plurality of interwoven fibers, mono-filaments, multi-filaments, or yarns. The graft layer 26 may include polyethylene terephthalate (PET), expanded polytetrafluoroethylene (ePTFE), polycarbonate urethane (PCU), polyurethane (PU), or combinations thereof. The membrane layer 30 may include siloxane polymers, polyurethane polymers, polycarbonate urethanes, PTFE, ePTFE, or combinations thereof. The membrane layers 30 may be a film, sheet, or tube. The stent-graft-membrane 20 substantially excludes a first fluid located outside the stent-graft-membrane 20 from reaching a second fluid located in the lumen 38.

Another preferred embodiment of the stent-graft-membrane includes one or more outside layers disposed over or on the outside of the stent 22. The outside layer is a membrane 30 made of a silicone or a polycarbonate urethane material that is biocompatible with the body tissue. One or more inside layers are disposed over or on the inside of the stent 22. The inside layer is a graft 26 made of braided PET material biocompatible with the fluid in the passage 38. The graft 26 may be braided, spun or spray-cast. The outside layers are substantially impermeable to a fluid and substantially separate a first body fluid located outside the stent-graft-membrane 20 from a second body fluid located in the passage 38.

Figure 7:
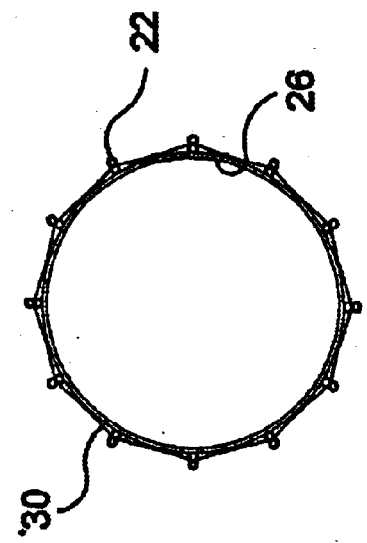

FIG. 7 illustrates an end view of a stent-graft-membrane 20 in which the inside layer is a graft layer 26 made of braided PET, the middle layer is a braided stent 22, and the outer layer is a membrane layer 30 made of silicone. The composite layers include three-layers 22, 26, 30 which may be bonded together under heat and pressure so that the membrane layer 30 conforms to the profile of the stent layer 22 and graft layer 26 as shown.

Figure 8:
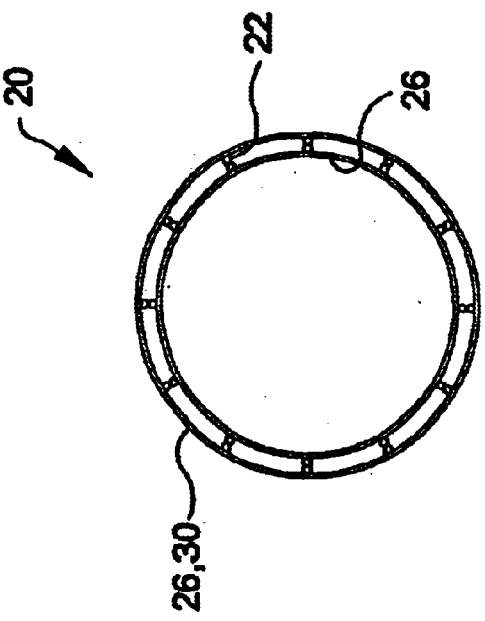
FIGS. 7–8 illustrate end views of two embodiments of the stent-graft-membrane.

FIG. 8 illustrates a stent-graft-membrane 20. The inside layer is a graft layer 26 made of braided PET. The middle layer is a braided stent 22. The outside layer is a graft layer 26 made of braided PET which has been impregnated with silicone to create a substantially impermeable graft/membrane layer 26, 30 as described in Example 1.

Figure 9:
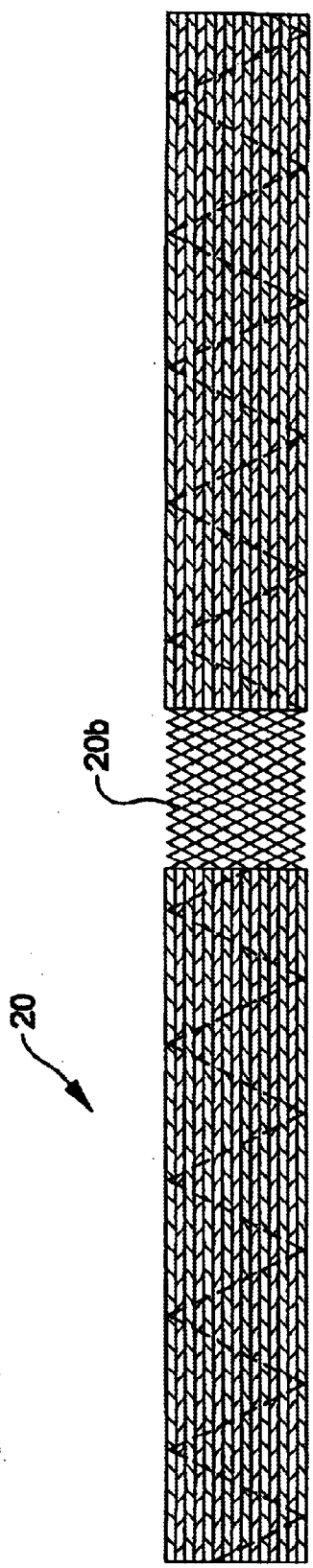
FIG. 9 illustrates a side view of an embodiment of the stent-graft-membrane with an exposed middle portion.
Figure 10:
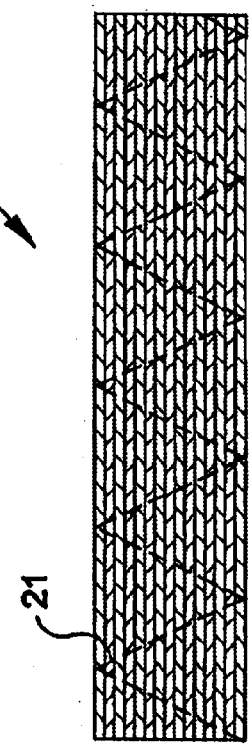
FIG. 10 illustrates a side view of an embodiment of a fully covered stent-graft-membrane.
Figure 11:
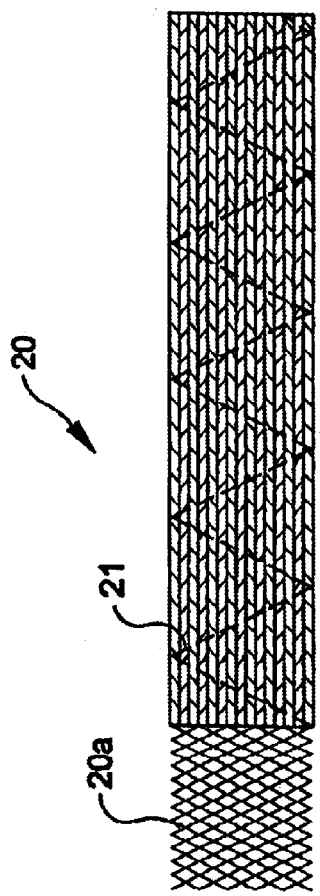
FIG. 11 illustrates a side view of an embodiment of the stent-graft-membrane with one exposed end portion.
Figure 12:
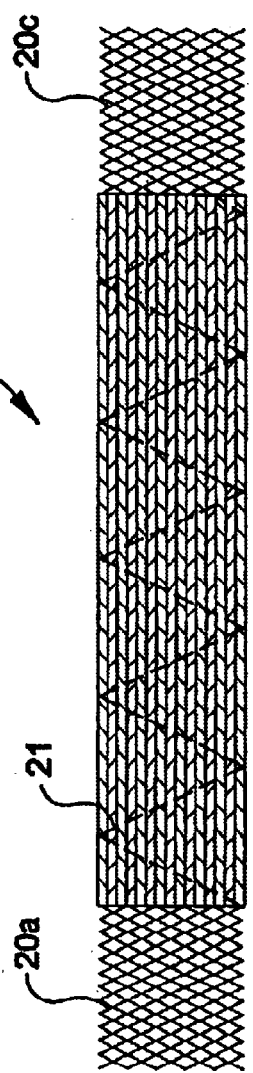
FIG. 12 illustrates a side view of an embodiment of the stent-graft-membrane with two exposed end portions.

Various portions of the stent-graft-membrane 20 may be covered by the graft 26 or membrane 30. For example, FIG. 9 illustrates a stent-graft-membrane 20 with an exposed middle portion 20b. FIG. 10 illustrates a fully covered stent-graft-membrane 20. FIG. 11 illustrates a stent-graft-membrane 20 with one exposed end portion 20a FIG. 12 illustrates a stent-graft-membrane 20 with two exposed end portions 20a, 20c.

Figure 13:
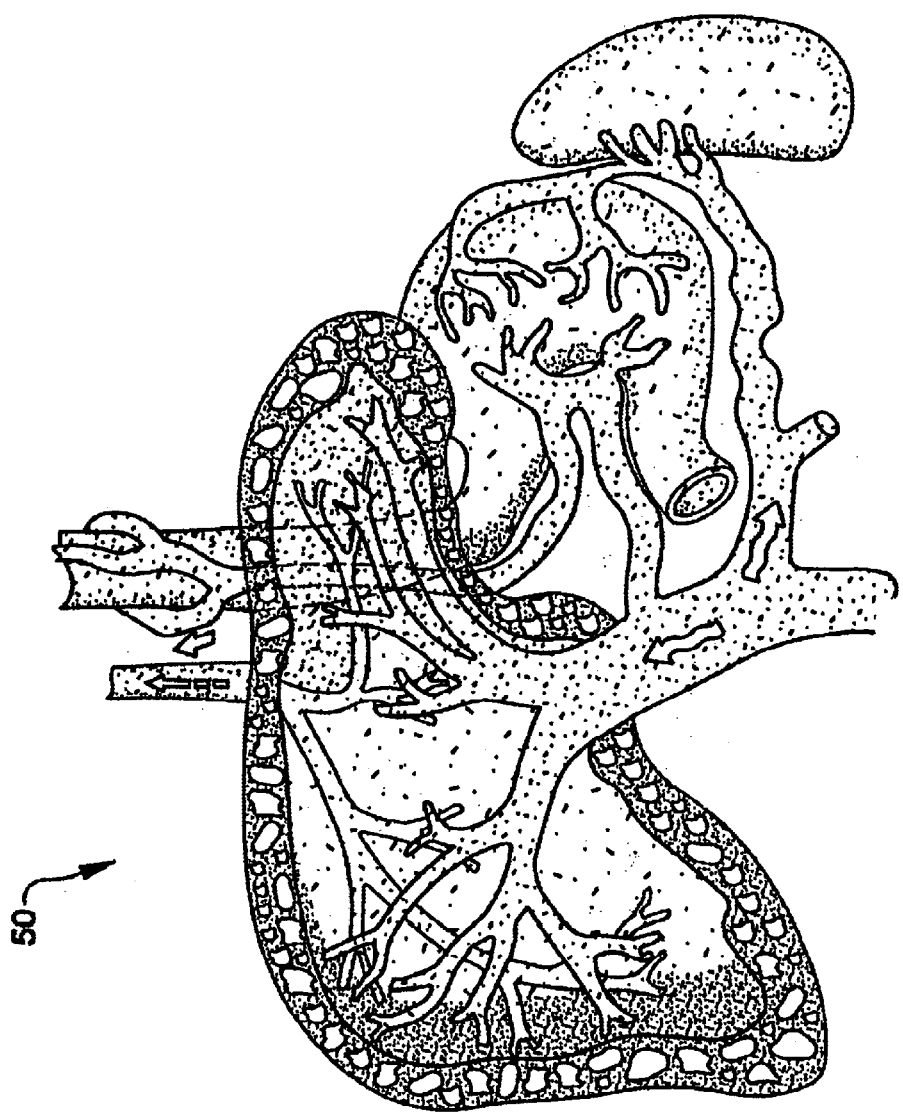
FIG. 13 illustrates a TIPS treatment site.
Figure 14:
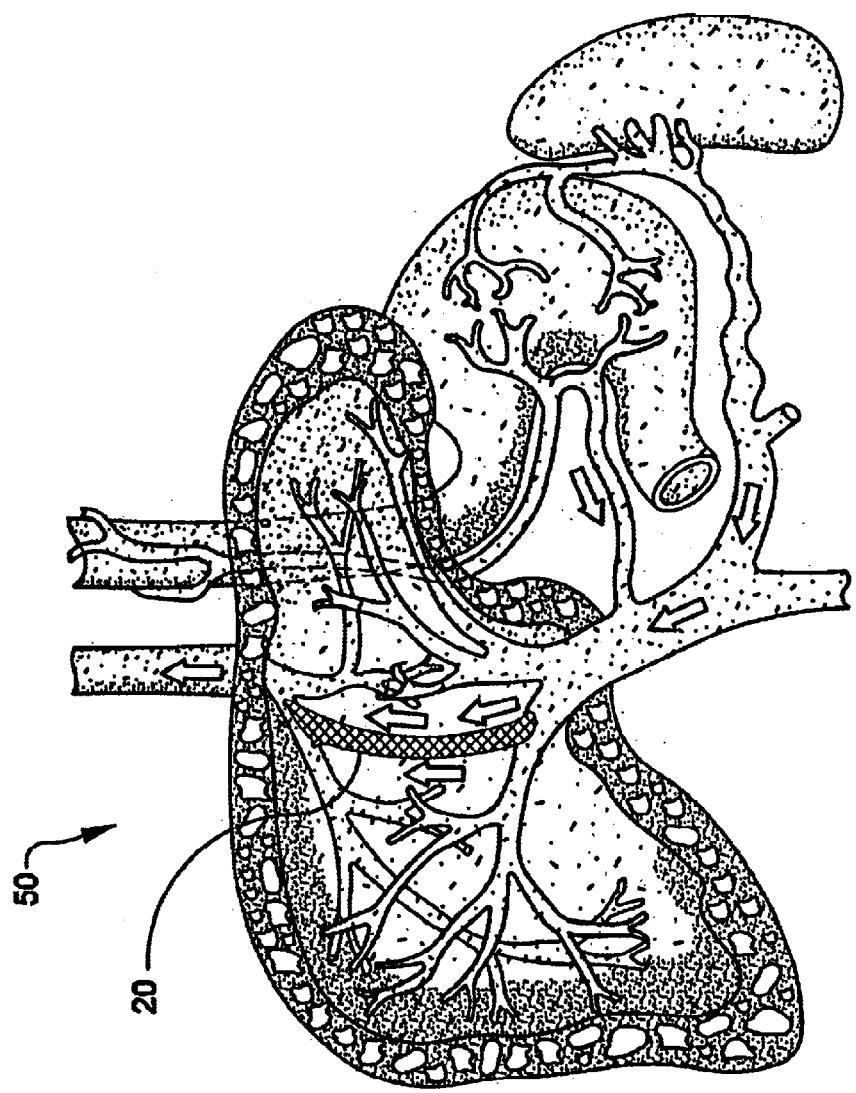
FIG. 14 illustrates a stent-graft-membrane at a TIPS treatment site.

FIG. 13 illustrates a TIPS treatment site 50. FIG. 14 illustrates a stent-graft-membrane 20 disposed at a TIPS treatment site 50. The stent-graft-membrane 20 may be used for creation or revision of a transjugular intrahepatic portosystemic shunt (TIPS). The stent-graft-membrane 20 substantially separates a first fluid such as bile located outside the stent-graft-membrane 20 from a second fluid such as blood located and channeled in the passage 38. One end portion of the stent-graft-membrane 20 is disposed in a portal vein, a middle portion of the stent-graft-membrane 20 is disposed in a liver, and the other end portion is disposed in a hepatic vein.

A TIPS treatment method includes puncturing the right internal jugular vein; advancing a wire into the IVC followed by a 40 cm, 9–10F sheath with a hemostatic valve; catheterizing the hepatic vein; using a stiff wire to introduce the needle set; positioning the needle in the hepatic vein and retracting the sheath to reveal the needle tip; advancing the needle through the liver and puncturing the portal vein; injecting contrast to identify the vascular structure; advancing a guidewire through the needle; the wire should enter the portal vein; removing the needle; introducing a catheter; measuring portal pressure; performing a portal venogram; exchanging the. catheter for a balloon; dilating the parenchymal tract; advancing the vascular sheath into the tract and removing the balloon; introducing the stent-graft-membrane into the portal vein; positioning and deploying the stent-graft-membrane; exchanging the delivery sheath for a 5Fr, 8 mm balloon; expanding the stent-graft-membrane; repeating the venogram and pressure measurement; and dilating if necessary. The sizes of the equipment and stent-graft-membrane used in the TIPS procedure may vary.

The above described embodiments of the invention are merely descriptive of its principles and are not to be considered limiting. Further modifications of the invention herein disclosed will occur to those skilled in the respective arts and all such modifications are deemed to be within the scope of the invention as defined by the following claims.

What is claimed is:

1. A body compatible endoprosthesis, including:
a tubular body including a graft layer formed of a graft material and having a graft layer surface that forms an inside surface of the tubular body and defines a fluid passage in the tubular body, wherein the graft layer has a first average permeability and is biocompatible with a first fluid contained in the fluid passage;
wherein the tubular body further includes a tubular structural layer comprising first and second sets of filaments helically wound in respective first and second different directions, and having a structural strength sufficient to maintain the fluid passage open in opposition to radially inward forces due to surrounding tissue; and
wherein the tubular body further includes a membrane layer formed of a membrane material, substantially surrounding the graft layer, and having a second average permeability of at most about 100 $cc/cm^2/min.$ at 120 mm Hg. and less than the first average permeability.

2. The endoprosthesis of claim 1 wherein:
the tubular body is radially reducible to a reduced diameter, and enlargeable to an increased diameter.

3. The endoprosthesis of claim 2 wherein:
the tubular body is constrainable to a reduced diameter and self-expandable to an increased diameter.

4. The endoprosthesis of claim 1 wherein:
the tubular body is adapted for deployment at a treatment site along body tissue, the membrane layer has a membrane layer surface that forms an outside surface of the tubular body adapted to contact the body tissue upon said deployment, and the membrane layer is biocompatible with said body tissue.

5. The endoprosthesis of claim 1 wherein:

said first average permeability of the graft material layer is within a range from about 50 cc/cm$^2$/min. to about 5,000 cc/cm$^2$/min. at 120 mm Hg.

6. The endoprosthesis of claim 1 wherein:

said membrane material comprises at least one material from the group consisting of: silicone elastomers, polyurethane polymers, polycarbonate urethanes, polytetrafluoroethylene (PTFE), and ePTFE.

7. The endoprosthesis of claim 6 wherein:

said membrane material is a silicone elastomer.

8. The endoprosthesis of claim 1 wherein:

said graft material comprises at least one of the materials selected from the group consisting of: polyethylene terepthalate (PET), polytetrafluoroethylene (PTFE), expanded polytetrafluoroethylene (PTFE), polycarbonate urethane, polyurethane, polypropylene, polyethylene, silicone, and polyolefins.

9. The endoprosthesis of claim 8 wherein:

the graft material is polyethylene terepthalate (PET).

10. The endoprosthesis of claim 1 wherein:

the membrane layer is configured to substantially isolate the first fluid contained in the fluid passage from a second fluid located outside the tubular body.

11. The endoprosthesis of claim 10 wherein:

the first fluid comprises blood, and the second fluid comprises bile.

12. The endoprosthesis of claim 11 wherein:

said tubular body is adapted to be deployed at a transjugular intrahepatic portal systemic shunt (TIPS) treatment site.

13. The endoprosthesis of claim 1 wherein:

the structural layer is disposed between the membrane layer and the graft layer.

14. The endoprosthesis of claim 1 wherein:

said membrane layer is formed by coating the structural layer with the membrane material.

15. The endoprosthesis of claim 1 wherein:

the membrane layer consists essentially of a porous layer formed of a graft material and impregnated with the membrane material.

16. An implantable endoprosthesis comprising:

a tubular support structure defining a longitudinal passage extending therethrough, and having sufficient structural strength to maintain the longitudinal passage open in opposition to radially inward forces due to surrounding tissue;

a membrane made of a membrane material disposed on at least a portion of the outside of the tubular support structure;

a graft layer disposed on at least a portion of the inside of the tubular support structure;

wherein the graft layer has a first average permeability ranging from about 50 to about 5,000 cc/cm$^2$/min. at 120 mm Hg. and is adapted for containing a first fluid in the passage, and the membrane has a second average permeability less than the first average permeability of at most about 100 cc/cm$^2$/min. at 120 mm. Hg., and is adapted for isolating the first fluid in the passage from a second fluid located outside the passage.

17. The endoprosthesis of claim 16 wherein:

the first fluid consists essentially of blood, and the second fluid consists essentially of bile.

18. The endoprosthesis of claim 16 wherein:

the membrane consists essentially of a coating of a membrane material applied to the tubular support structure.

19. The endoprosthesis of claim 16 wherein:

the membrane consists essentially of a porous layer formed of a graft material and coated with the membrane material.

20. The endoprosthesis of claim 16 wherein:

said support structure comprises first and second sets of filaments wound helically in respective and different first and second directions, crossing one another to form multiple crossing points.

21. The endoprosthesis of claim 20 wherein:

the support structure is constrainable to a reduced diameter and self-expandable to an increased diameter.

22. A process for making an implantable endoprosthesis, including:

providing a tubular support structure defining a longitudinal passage, and having sufficient structural strength to maintain the passage open in opposition to radially inward forces due to surrounding tissue;

forming a graft layer of a graft material with a first average permeability, and disposing the graft layer along an inside surface of the tubular support structure; and coating the tubular support structure with a membrane material to form a membrane layer, with a second average permeability of the membrane layer being less than the first average permeability of the graft layer.

23. The process of claim 22 wherein:

the forming of the membrane layer further comprises disposing a porous layer of a graft material along an outside surface of the support structure, and coating the support structure and the porous layer with the membrane material.

24. A body insertable prosthesis, including:

a tubular body including a structural layer adapted to maintain the tubular body open in opposition to radially inward forces due to surrounding tissue, a graft layer formed of a graft material having a first average permeability ranging from about 50 to about 5,000 cc/cm$^2$/min. at 120 mm Hg., and a membrane layer formed of a membrane material, disposed outwardly of the graft layer and having a second average permeability less than the first average permeability and at most about 100 cc/cm$^2$/min. at 120 mm. Hg.

25. The prosthesis of claim 24 wherein:

the tubular body is constrainable to a reduced diameter and self-expandable to an increased diameter.

26. The prosthesis of claim 24 wherein:

the structural layer comprises a plurality of wound filaments crossing one another to form multiple crossing points.

27. The prosthesis of claim 26 wherein:

the plurality of filaments comprise first and second sets of the filaments wound helically in respective first and second different common directions.

28. The prosthesis of claim 24 wherein:

the membrane layer consists essentially of a porous layer formed of a graft material and either impregnated with or coated with the membrane material.

29. The prosthesis of claim 24 wherein:

the structural layer is disposed between the membrane layer and the graft layer.

* * * * *